(12) United States Patent
Santaana-Dela Rosa

(10) Patent No.: US 6,988,998 B1
(45) Date of Patent: Jan. 24, 2006

(54) DYNAMIC DORSAL-BLOCKING ADJUSTABLE SPLINT

(76) Inventor: Horacio Santaana-Dela Rosa, 4700 Heather Ridge Rd., Oakdale, MN (US) 55128

(*) Notice: Subject to any disclaimer, the term of this patent is extended or adjusted under 35 U.S.C. 154(b) by 0 days.

(21) Appl. No.: 11/036,323

(22) Filed: Jan. 18, 2005

(51) Int. Cl.
 *A51F 5/00* (2006.01)
(52) U.S. Cl. .......................... 602/20; 602/21; 602/60; 602/61
(58) Field of Classification Search ................ 602/20, 602/21, 22, 60, 61, 64; 2/161.7, 159; 482/44, 482/47, 48
See application file for complete search history.

(56) References Cited

U.S. PATENT DOCUMENTS

| | | | |
|---|---|---|---|
| 1,728,679 A * | 9/1929 | Hansard | 473/213 |
| 1,817,212 A * | 8/1931 | Siebrandt | 602/21 |
| 3,152,337 A * | 10/1964 | Barry | 2/159 |
| 3,262,126 A * | 7/1966 | Price | 2/159 |
| 3,347,547 A * | 10/1967 | Hynes | 482/47 |
| 3,714,940 A * | 2/1973 | Palmer | 602/21 |
| 3,756,222 A * | 9/1973 | Ketchum | 601/40 |
| 4,456,002 A | 6/1984 | Barber et al. | |
| 4,602,620 A * | 7/1986 | Marx | 602/21 |
| 4,644,938 A * | 2/1987 | Yates et al. | 601/40 |
| 4,840,168 A | 6/1989 | Lonardo | |
| 4,875,469 A * | 10/1989 | Brook et al. | 601/40 |
| 4,945,902 A * | 8/1990 | Dorer et al. | 602/38 |
| 5,203,766 A * | 4/1993 | Carter et al. | 602/21 |
| 5,230,699 A | 7/1993 | Grasinger | |
| 5,324,251 A | 6/1994 | Watson | |
| 5,328,448 A * | 7/1994 | Gray, Sr. | 602/22 |
| 5,376,066 A | 12/1994 | Phillips et al. | |
| 5,413,554 A * | 5/1995 | Trueman | 602/21 |
| 5,538,488 A * | 7/1996 | Villepigue | 482/47 |
| 5,643,186 A * | 7/1997 | Chinchalkar | 602/32 |
| 5,820,577 A * | 10/1998 | Taylor | 601/40 |
| 5,957,813 A * | 9/1999 | Macdonald | 482/44 |
| 6,063,087 A * | 5/2000 | Agee et al. | 606/55 |
| 6,093,162 A * | 7/2000 | Fairleigh et al. | 602/22 |
| D456,081 S | 4/2002 | Bell et al. | |
| 6,458,091 B1 | 10/2002 | Parker et al. | |
| 6,565,563 B1 * | 5/2003 | Agee et al. | 606/55 |

\* cited by examiner

*Primary Examiner*—Henry Bennett
*Assistant Examiner*—Dinnatia Doster-Greene

(57) ABSTRACT

A splint positionable about a user's hand for treating phalanx fractures includes a flexible body having a first opening for receiving a thumb therethrough and a second opening for allowing selected metacarpals to extend distally therethrough. The present invention further includes a mechanism for maintaining the end portions at selected spatial relationships and a flexible aluminum plate for engaging fractured metacarpals while allowing medial and distal metacarpal phalangeal joints to move along unrestricted paths respectively. The splint further includes a mechanism for adjusting a length of the plate so that the fractured metacarpals can be adapted between mobile and immobile positions.

18 Claims, 4 Drawing Sheets

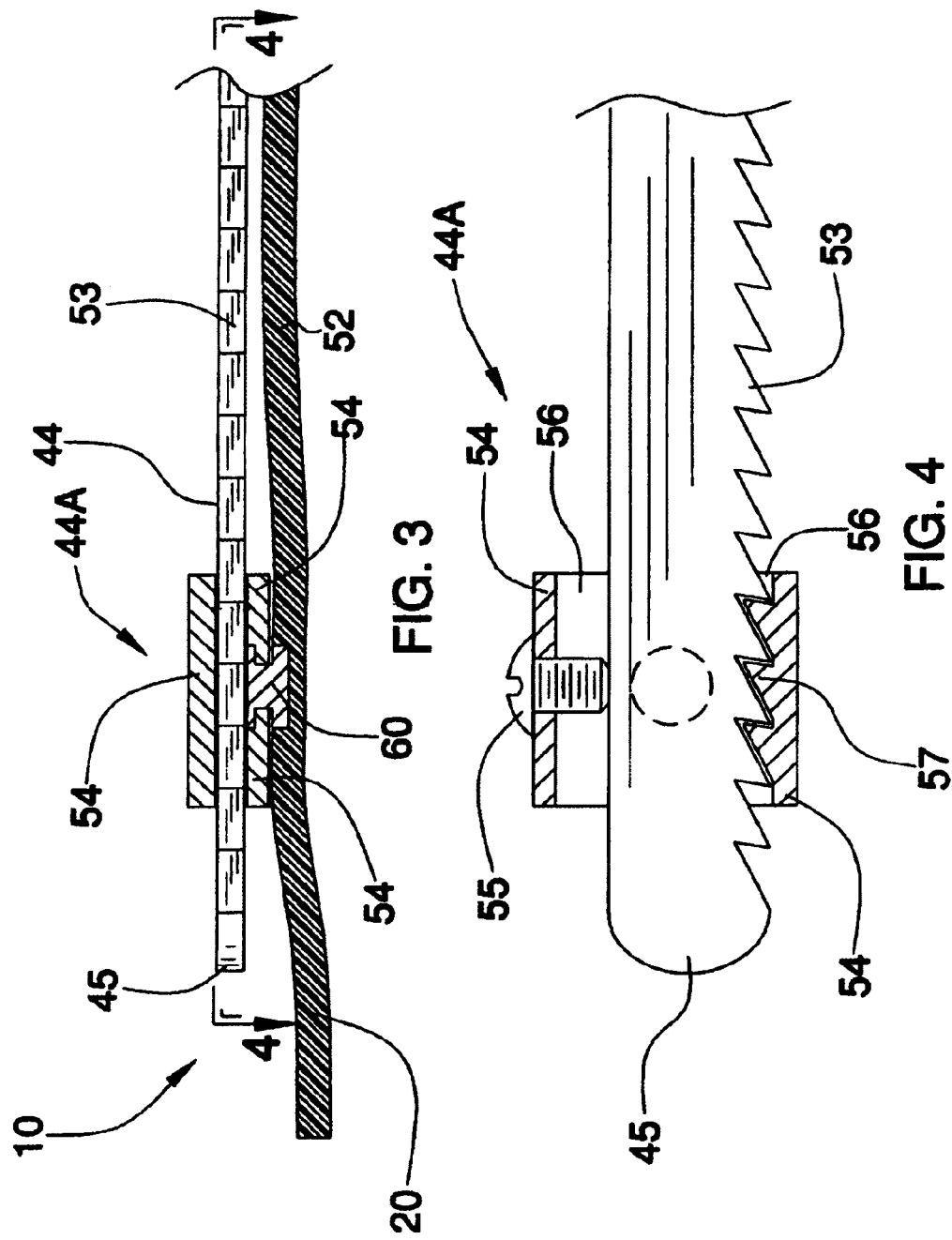

DYNAMIC DORSAL-BLOCKING ADJUSTABLE SPLINT

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to a phalanx splint and, more particularly, to an adjustable phalanx splint for treating phalanx fractures.

2. Prior Art

Fractures of a finger's middle or proximal phalanx have traditionally been immobilized in a reduced position in one of two ways. One approach is surgical in nature and involves the insertion of pins or screws to stabilize or reduce the fracture. A second, non-surgical approach, involves casting the hand, wrist and distal forearm in cooperation with an outrigger splint to hold the fractured finger. However, each of these approaches is inherently flawed in that each fosters various medical side effects that may necessitate further medical treatment.

For example, the surgical approach traumatizes the surrounding tissue, muscles and bone structure, thereby increasing the amount of post operative therapy required for proper healing. In addition, surgery always introduces the possibility of infection. The non-surgical splint approach requires that the finger be splinted in a crooked position in order to prevent the finger's extensor tendons from causing the fracture to angulate.

This approach has two major drawbacks. First, immobilization of the fracture in a properly reduced position also inconveniently immobilizes the patient's hand. Secondly, immobilizing the finger in the crooked position pulls the extensor tendon onto the healing fracture. This may cause the callus formed during healing to adhere to the extensor tendon. Therefore, once the splint is removed, it is sometimes necessary to surgically release the tendon from the newly formed bone. Furthermore, even if such surgery is not required, joints adjacent to the fracture stiffen while the finger is splinted. Accordingly, some therapy is required to restore the finger's flexing mobility once the cast and splint are removed.

Accordingly, a need remains for an adjustable phalanx splint to overcome the above noted shortcomings. The present invention satisfies such a need by providing a splint that is easy to use, has an adjustable design, is comfortable to wear, and has advanced healing benefits. Such a splint provides dynamic immobilization of a fractured finger while ensuring movement and flexibility in unaffected areas of the hand. The adjustable phalanx splint would be appreciated by hand surgeons, orthopedic doctors, general practitioners and emergency rooms where its use would greatly benefit all parties involved.

BRIEF SUMMARY OF THE INVENTION

In view of the foregoing background, it is therefore an object of the present invention to provide an apparatus for an adjustable phalanx splint. These and other objects, features, and advantages of the invention are provided by a splint positionable about a user's hand for treating phalanx fractures.

The splint includes a flexible body formed from durable material and sized and shaped for being removably positionable about the user's hand. Such a body has a first opening for distally receiving a user's thumb therethrough and further has opposed end portions disposed proximally to the first opening and parallel to a longitudinal plane extending along a top surface of the user's hand. The body further has a second opening spaced from the first opening for allowing selected metacarpals to extend distally therethrough and away from the end portions.

The present invention further includes a mechanism for adjustably maintaining the end portions at selected spatial relationships so that a user can advantageously readily apply and remove the splint as needed. The maintaining mechanism preferably includes a pair of rigid support members integrally disposed along the body end portions respectively and situated substantially parallel to the axis. Such support members are provided with a plurality of spaced apertures aligned along a length thereof respectively. A plurality of fastening members are threadably insertable through associated pairs of the support member apertures so that the body can be securely retrofitted about the user's hand.

A flexible aluminum plate is included which is adaptable to selected shapes and has opposed corner portions. The flexible aluminum plate further has three lines of weakness dividing the plate into four sections and being held by a clamp having opposed end portions and a substantially U-shape. The four sections immobilize one to four fingers at a time, or as many as needed. Three sections of the aluminum plate may be articulated such that the clamp can be reshaped according to the user's needs.

Such a plate engages fractured metacarpals along a path substantially transverse to the axis so that associated metacarpal phalangeal joints will be effectively maintained at approximately 90 degrees offset counterclockwise from the axis. This conveniently allows medial and distal metacarpal phalangeal joints to move along unrestricted paths respectively. The plate preferably further includes a bottom layer formed from resilient foam material and extending along a length thereof. Such a bottom layer is positionable against the user's fractured phalangeal joints for conveniently providing comfort thereto when the splint is worn during extended periods of use.

The splint further includes a mechanism for adjusting a length of the plate so the fractured metacarpals can be adapted between mobile and immobile positions. The clamp end portions preferably have serrated edges extending obliquely therefrom and situated medially towards a center of the user's palm. The adjusting mechanism includes a plurality of brackets secured to a proximal end portion of the body and adjacent to the user's palm. A plurality of fastening members are threadably engageable through the brackets for effectively assisting to maintain the clamp end portions at a substantially stable position.

Such brackets are oppositely spaced apart from the axis and include a plurality of rectilinear passageways provided with associated finger portions for locking and engaging the serrated edges respectively. The finger portions are integral with the brackets for advantageously limiting movement of the clamp end portions along a predetermined direction and cooperating with the brackets to effectively maintain the user's fractured phalangeal joints at the selected angle during operating conditions.

The splint may further include a plurality of pin members pivotally connected to the brackets and the body respectively so that the clamp can be selectively pivoted along straight paths and advantageously provide tolerable movement of the user's fractured phalangeal joint.

The maintaining mechanism preferably includes a pair of rigid support members integrally disposed along the body end portions respectively and situated substantially parallel to the axis. Such support members are provided with a plurality of spaced apertures aligned along a length thereof respectively. A plurality of fastening members are threadably insertable through associated pairs of the support member apertures so that the body can be securely retrofitted about the user's hand.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 3 is a cross-sectional view of the apparatus shown in FIG. 2, taken along line 3—3;

FIG. 4 is an enlarged cross-sectional view of the apparatus shown in FIG. 3, taken along line 4—4;

DETAILED DESCRIPTION OF THE INVENTION

Figure 1:
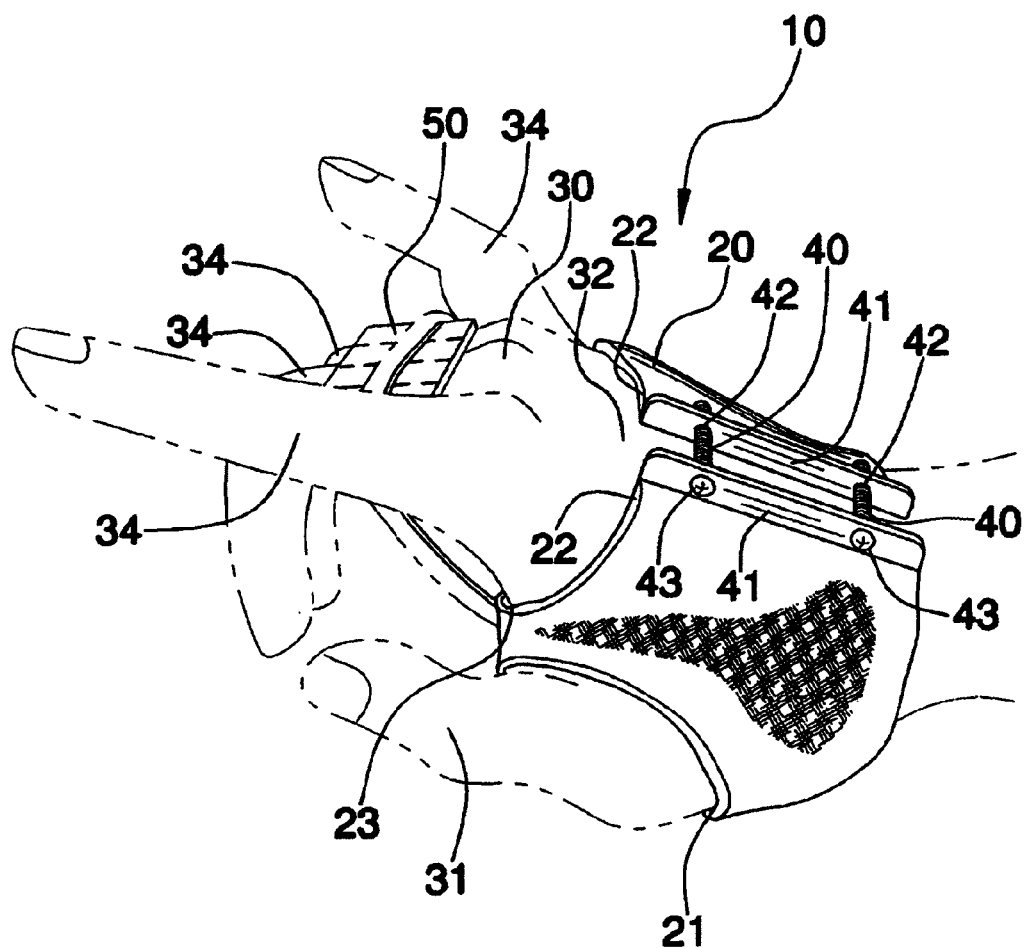
FIG. 1 is a perspective view showing an apparatus for an adjustable phalanx splint, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1–6 by the reference numeral 10 and is intended to provide an adjustable phalanx splint. It should be understood that the apparatus 10 may be used to splint various combinations of one to four metacarpals and should not be limited to splinting only one metacarpal.

Referring initially to FIG. 1, the apparatus 10 includes a flexible body 20 formed from durable material and sized and shaped for being removably positionable about the user's hand 30. Such a body 20 has a first opening 21 for distally receiving a user's thumb 31 therethrough and further has opposed end portions 22 disposed proximal to the first opening 21 and parallel to a longitudinal plane extending along a top surface 32 of the user's hand 30. The body 20 further has a second opening 23 spaced from the first opening 21 for allowing selected metacarpals 34 to extend distally therethrough and away from the end portions 22.

Still referring to FIG. 1, the present invention further includes a mechanism 40 for adjustably maintaining the end portions 22 at selected spatial relationships so that a user can advantageously readily apply and remove the splint 10 as needed, conveniently eliminating the need for the hand 30 to be put in a permanent cast. The maintaining mechanism 40 includes a pair of rigid support members 41 integrally disposed along the body end portions 22 respectively and situated substantially parallel to the axis. Such support members 41 are provided with a plurality of spaced apertures 42 aligned along a length thereof respectively. A plurality of fastening members 43 are threadably insertable through associated pairs of the support member apertures 42 so that the body 20 can be securely retrofitted about the user's hand 30.

Figure 2:
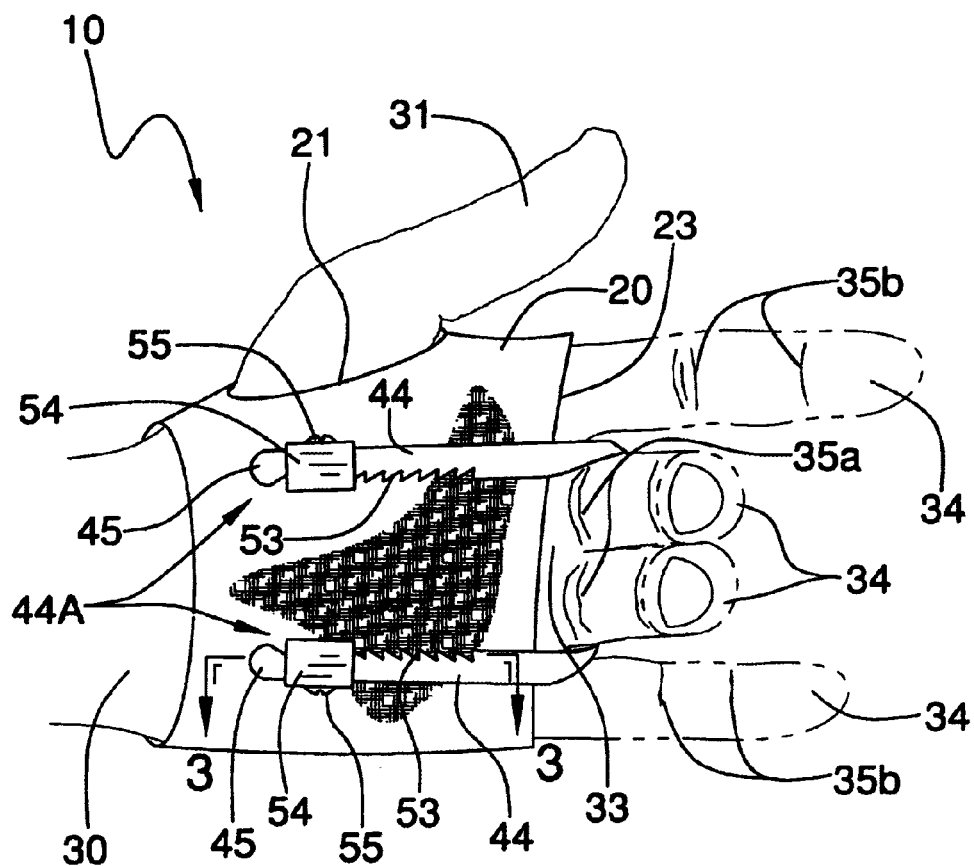
FIG. 2 is a bottom plan view of the apparatus shown in FIG. 1.
Figure 5:
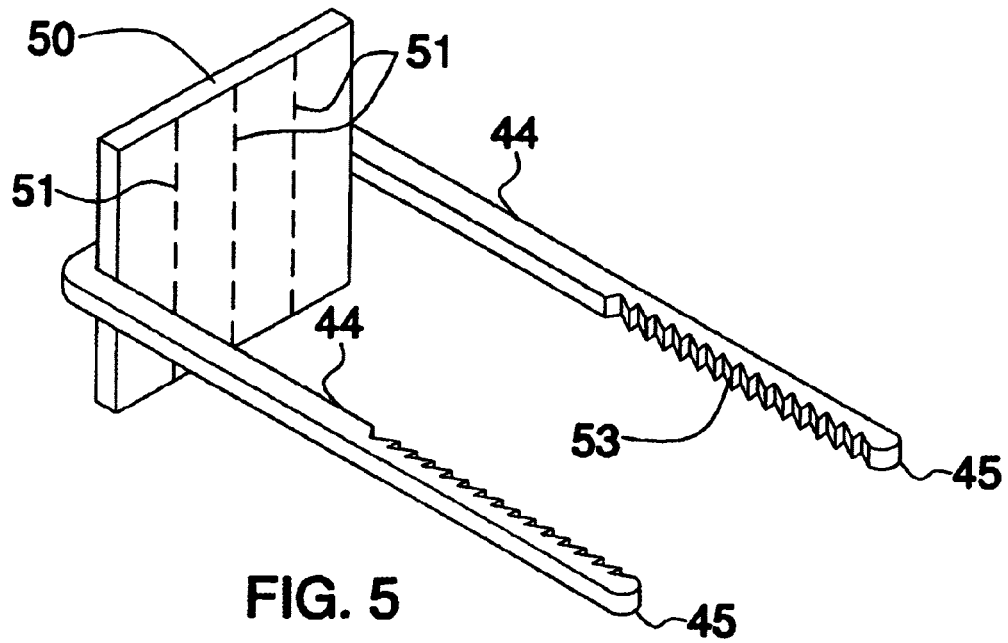
FIG. 5 is an enlarged perspective view of the flexible aluminum plate and clamp with serrated edges.
Figure 6:
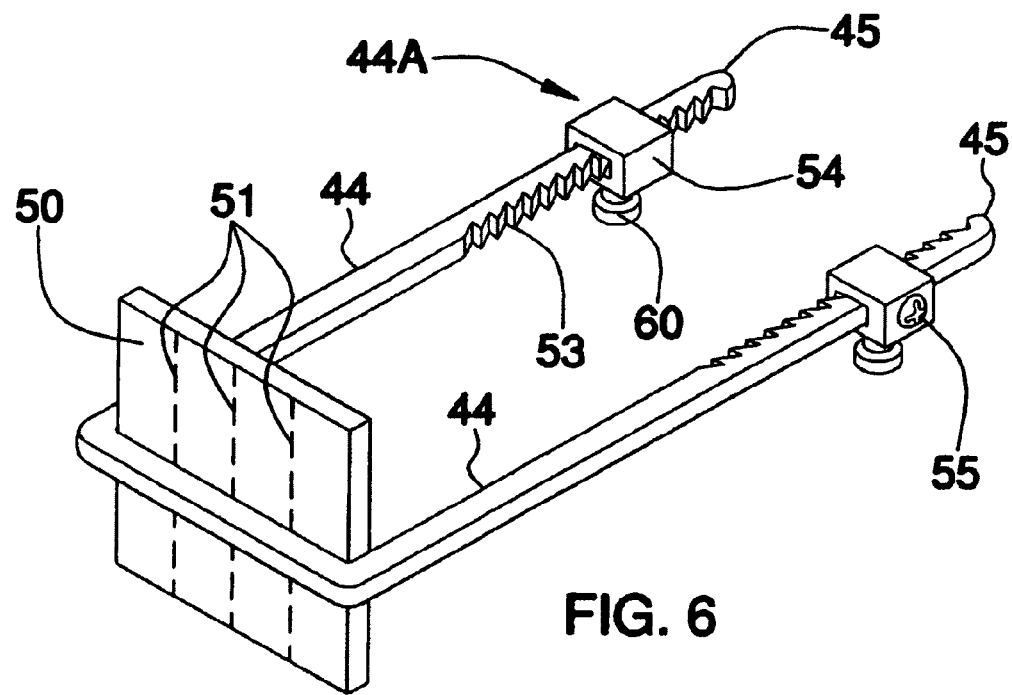
FIG. 6 is an enlarged perspective view of the flexible aluminum plate and clamp shown in FIG. 5, illustrating the brackets and fastening members.

Referring to FIGS. 2, 5, and 6, a flexible aluminum plate 50 is included which is adaptable to selected shapes. The aluminum plate 50 has three lines of weakness 51 dividing the plate 50 into four equal parts. Such a plate 50 is held in place by a serrated clamp 44 having a substantial U-shape. The clamp 44 further has opposed end portions 45 proximally spaced from a user's palm 33. Such a plate 50 engages fractured metacarpals 34 along a path substantially transverse to the axis so that associated metacarpal 34 phalangeal joints 35a will be effectively maintained at approximately 90 degrees offset counterclockwise from the axis. This conveniently allows medial and distal metacarpal 34 phalangeal joints 35b to move along unrestricted paths respectively.

Referring to FIG. 3, the plate 50 further includes a bottom layer 52 formed from resilient foam material and extending along a length thereof. Such a bottom layer 52 is positionable against the user's fractured phalangeal joints 35a for conveniently providing comfort thereto when the splint 10 is worn during extended periods of use. The bottom layer 52 advantageously increases the period of time the apparatus 10 can be worn comfortably. It also allows a user to wear it more often, thus shortening the overall healing time of the fractures.

Referring to FIGS. 2, 4, 5, and 6, the splint 10 further includes a mechanism 44A for adjusting a length of the clamp 44 so that the fractured metacarpals can be adapted between mobile and immobile positions. The ability to adjust the length of the clamp 44 advantageously allows it to be used on hands 30 of varying sizes and on multiple, as well as single, phalanx fractures. The clamp end portions 45 have serrated edges 53 extending obliquely therefrom and situated medially towards a center of the user's palm 33. The adjusting mechanism 44A includes a plurality of brackets 54 secured to a proximal end portion of the body 20 and adjacent to the user's palm 33. A plurality of fastening members 55 are threadably engageable through the brackets 54 for effectively assisting to maintain the clamp end portions 45 at a substantially stable position.

Still referring to FIG. 2, such brackets 54 are oppositely spaced apart from the axis and include a plurality of rectilinear passageways 56 provided with associated finger portions 57 for locking and engaging the serrated edges 53 respectively. The finger portions 57 are integral with the brackets 54 for advantageously limiting movement of the plate end portions 51 along a predetermined direction and cooperating with the brackets 54 to effectively maintain the user's fractured phalangeal joints 35*a* at the selected angle during operating conditions for optimal healing.

Referring to FIGS. 3 and 6, the splint 10 includes a plurality of bracket pin members 60 pivotally connected to the brackets 54 and the body 20 respectively so that the clamp 50 can slide sideways in a slot. The splint 10 includes one pin member 60 for each bracket 54 so the plate 50 can be moved according to the number of phalangeal fractures (one to four) to be immobilized and advantageously provide tolerable movement of the user's fractured phalangeal joint 35*a*.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A splint positionable about a user's hand and for treating phalanx fractures, said splint comprising:
    a flexible body sized and shaped for being removably positionable about the user's hand, said body having a first opening for distally receiving a user's thumb therethrough and further having opposed end portions disposed proximal to the first opening and parallel to a longitudinal plane extending along a top surface of the user's hand, said body further having a second opening spaced from the first opening for allowing selected metacarpals to extend distally therethrough and away from said end portions;
    means for maintaining said end portions at selected spatial relationships so that a user can readily apply and remove said splint as needed;
    a flexible aluminum plate having opposed corner portions and for engaging fractured metacarpals along a path substantially transverse to an axis so that associated metacarpal phalangeal joints will be maintained at a selected angle offset from the axis while allowing medial and distal metacarpal phalangeal joints to move along an unrestricted paths respectively;
    a clamp having opposed end portions adapted to be spaced across a user's palm, said clamp further having a substantially U-shape; and
    means for adjusting a length of said clamp so that the fractured metacarpals can be adapted between mobile and immobile positions.

2. The splint of claim 1, wherein said clamp end portions have serrated edges extending obliquely thereto and adapted to be situated medially towards a center of the user's palm, said adjusting means comprising a plurality of brackets adapted to be secured to a proximal end portion of said body and adjacent the user's palm, said brackets being oppositely spaced apart from the axis and including a plurality of rectilinear passageways provided with associated finger portions for locking engaging said serrated edges respectively, said finger portions being integral with said brackets for limiting movement of said clamp end portions along a predetermined direction and cooperating with said brackets to maintain the user's fractured phalangeal joints at the selected angle during operating conditions.

3. The splint of claim 2, further comprising a plurality of pin members pivotally connected to said brackets and said body respectively so that said clamp can be selectively pivoted along straight paths and provide tolerable movement of the user's fractured phalangeal joints.

4. The splint of claim 2, further comprising a plurality of fastening members threadably engageable through said brackets and for assisting to maintain said clamp end portions at substantially stable positions.

5. The splint of claim 1, wherein said plate further comprises: a bottom layer formed from resilient foam material and extending along a length thereof, said bottom layer being positionable against the user's fractured phalangeal joints for providing comfort thereto when said splint is worn during extended periods of use.

6. The splint of claim 1, wherein said maintaining means comprises:
    a pair of rigid support members integrally disposed along said body end portions respectively and situated substantially parallel to the axis, said support members being provided with a plurality of spaced apertures aligned along a length thereof respectively; and
    a plurality of fastening members threadably insertable through associated pairs of the support member apertures so that said body can be securely retrofitted about the user's hand.

7. A splint positionable about a user's hand and for treating phalanx fractures, said splint comprising:
    a flexible body formed from durable material and sized and shaped for being removably positionable about the user's hand, said body having a first opening for distally receiving a user's thumb therethrough and further having opposed end portions disposed proximal to the first opening and parallel to a longitudinal plane extending along a top surface of the user's hand, said body further having a second opening spaced from the first opening for allowing selected metacarpals to extend distally therethrough and away from said end portions;
    means for adjustably maintaining said end portions at selected spatial relationships so that a user can readily apply and remove said splint as needed;
    a flexible aluminum plate having opposed end corners and for engaging fractured metacarpals along a path substantially transverse to an axis so that associated metacarpal phalangeal joints will be maintained at approximately 90 degrees offset counterclockwise from the axis while allowing medial and distal metacarpal phalangeal joints to move along unrestricted paths respectively;
    a clamp having opposed end portions adapted to be spaced across a user's palm, said clamp further having a substantially U-shape; and
    means for adjusting a length of said clamp so that the fractured metacarpals can be adapted between mobile and immobile positions.

8. The splint of claim 7, wherein said clamp end portions have serrated edges extending obliquely therefrom and adapted to be situated medially towards a center of the user's palm, said adjusting means comprising a plurality of brackets adapted to be secured to a proximal end portion of said body and adjacent the user's palm, said brackets being oppositely spaced apart from the axis and including a plurality of rectilinear passageways provided with associated finger portions for locking engaging said serrated edges respectively, said finger portions being integral with said brackets for limiting movement of said plate end portions along a predetermined direction and cooperating with said brackets to maintain the user's fractured phalangeal joints at the selected angle during operating conditions.

9. The splint of claim 8, further comprising a plurality of pin members pivotally connected to said brackets and said body respectively so that said plate can be selectively pivoted along straight paths and provide tolerable movement of the user's fractured phalangeal joints.

10. The splint of claim 8, further comprising a plurality of fastening members threadably engageable through said brackets and for assisting to maintain said clamp end portions at substantially stable positions.

11. The splint of claim 7, wherein said plate further comprises: a bottom layer formed from resilient foam material and extending along a length thereof, said bottom layer being positionable against the user's fractured phalangeal joints for providing comfort thereto when said splint is worn during extended periods of use.

12. The splint of claim 7, wherein said maintaining means comprises:
    a pair of rigid support members integrally disposed along said body end portions respectively and situated substantially parallel to the axis, said support members being provided with a plurality of spaced apertures aligned along a length thereof respectively; and
    a plurality of fastening members threadably insertable through associated pairs of the support member apertures so that said body can be securely retrofitted about the user's hand.

13. A splint positionable about a user's hand and for treating phalanx fractures, said splint comprising:
    a flexible body formed from durable material and sized and shaped for being removably positionable about the user's hand, said body having a first opening for distally receiving a user's thumb therethrough and further having opposed end portions disposed proximal to the first opening and parallel to a longitudinal plane extending along a top surface of the user's hand, said body further having a second opening spaced from the first opening for allowing selected metacarpals to extend distally therethrough and away from said end portions;
    means for adjustably maintaining said end portions at selected spatial relationships so that a user can readily apply and remove said splint as needed;
    a flexible aluminum plate being adaptable to selected shapes and having opposed end corners and for engaging fractured metacarpals along a path substantially transverse to an axis so that associated metacarpal phalangeal joints will be maintained at approximately 90 degrees offset counterclockwise from the axis while allowing medial and distal metacarpal phalangeal joints to move along an unrestricted paths respectively;
    a clamp having opposed end portions adapted to be spaced across a user's palm, said clamp further having a substantially U-shape; and
    means for adjusting a length of said clamp so that the fractured metacarpals can be adapted between mobile and immobile positions.

14. The splint of claim 13, wherein said clamp end portions have serrated edges extending obliquely therefrom and adapted to be situated medially towards a center of the user's palm, said adjusting means comprising a plurality of brackets adapted to be secured to a proximal end portion of said body and adjacent the user's palm, said brackets being oppositely spaced apart from the axis and including a plurality of rectilinear passageways provided with associated finger portions for locking engaging said serrated edges respectively, said finger portions being integral with said brackets for limiting movement of said clamp end portions along a predetermined direction and cooperating with said brackets to maintain the user's fractured phalangeal joints at the selected angle during operating conditions.

15. The splint of claim 14, further comprising a plurality of pin members pivotally connected to said brackets and said body respectively so that said clamp can be selectively pivoted along straight paths and provide tolerable movement of the user's fractured phalangeal joints.

16. The splint of claim 14, further comprising a plurality of fastening members threadably engageable through said brackets and for assisting to maintain said clamp end portions at substantially stable positions.

17. The splint of claim 13, wherein said plate further comprises: a bottom layer formed from resilient foam material and extending along a length thereof, said bottom layer being positionable against the user's fractured phalangeal joints for providing comfort thereto when said splint is worn during extended periods of use.

18. The splint of claim 13, wherein said maintaining means comprises:
    a pair of rigid support members integrally disposed along said body end portions respectively and situated substantially parallel to the axis, said support members being provided with a plurality of spaced apertures aligned along a length thereof respectively; and
    a plurality of fastening members threadably insertable through associated pairs of the support member apertures so that said body can be securely retrofitted about the user's hand.

* * * * *